(12) United States Patent
Matthiessen et al.

(10) Patent No.: US 7,578,293 B2
(45) Date of Patent: Aug. 25, 2009

(54) COMPRESSED AIR RESPIRATOR

(75) Inventors: Hans Matthiessen, Bad Schwartau (DE); Kai Kück, Hamburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 88 days.

(21) Appl. No.: 11/372,179

(22) Filed: Mar. 9, 2006

(65) Prior Publication Data
US 2006/0260612 A1 Nov. 23, 2006

(30) Foreign Application Priority Data
May 20, 2005 (DE) .................. 10 2005 023 393

(51) Int. Cl.
*A61M 16/00* (2006.01)

(52) U.S. Cl. .................. 128/205.17; 128/204.23; 128/204.26; 128/204.21; 128/205.13; 128/204.22; 128/204.18

(58) Field of Classification Search ............ 128/200.24, 128/203.12, 203.14, 203.25, 204.18, 204.21, 128/204.23, 204.26, 204.28, 205.13, 205.14, 128/205.15, 205.16, 205.17, 911, 203.13
See application file for complete search history.

(56) References Cited

U.S. PATENT DOCUMENTS 3,768,468 A * 10/1973 Cox .................. 128/204.21
3,913,576 A * 10/1975 Martin et al. .......... 128/204.25
3,951,137 A * 4/1976 Conkle et al. ............ 600/532
4,423,723 A * 1/1984 Winkler et al. ......... 128/202.22
4,622,976 A * 11/1986 Timpe et al. ............. 600/431
5,036,841 A * 8/1991 Hamilton ............. 128/202.26
5,398,675 A * 3/1995 Henkin et al. .......... 128/203.12
5,507,280 A * 4/1996 Henkin et al. .......... 128/203.12
5,509,406 A * 4/1996 Kock et al. ........... 128/203.14
5,678,540 A * 10/1997 Kock et al. ........... 128/205.13
5,857,458 A * 1/1999 Tham et al. ............ 128/203.28
6,003,513 A * 12/1999 Readey et al. ......... 128/205.24
6,123,072 A * 9/2000 Downs ................. 128/204.21
6,895,961 B1 * 5/2005 Todorov ............... 128/201.27
7,066,176 B2 * 6/2006 Jaffe et al. ............ 128/205.24

FOREIGN PATENT DOCUMENTS

GB 2 274 249 7/1994

* cited by examiner

*Primary Examiner*—Justin R Yu
*Assistant Examiner*—Annette F Dixon
(74) *Attorney, Agent, or Firm*—McGlew and Tuttle, P.C.

(57) ABSTRACT

A compressed air respirator has prolonged operating time due to a rebreathing feature. The respirator has a compressed air reserve (1) with a connected demand air supply valve (2), wherein the demand air supply valve (2) is connected with a reversible breathing gas reservoir (4) with adjustable volume. A rebreathing line (25) for the user of the apparatus has an expiration valve (88), wherein the rebreathing line (25) is connected with the breathing gas reservoir (4).

3 Claims, 3 Drawing Sheets

COMPRESSED AIR RESPIRATOR

CROSS REFERENCE TO RELATED APPLICATIONS

This application claims the benefit of priority under 35 U.S.C. § 119 of German Patent Application DE 10 2005 023 393.7 filed May 20, 2005, the entire contents of which are incorporated herein by reference.

FIELD OF THE INVENTION

The present invention pertains to a compressed air respirator.

BACKGROUND OF THE INVENTION

The drawback of the compact compressed air respirators used hitherto as rescue or escape apparatus is the fact that not only are nearly 80 vol. % of inert gases to be carried with the compressed air reserve available for breathing, which is carried by the user of the respirator, but also that only a few vol. % of the oxygen breathed in are utilized physiologically and the rest is blown off into the environment during breathing out. On the other hand, it is advantageous in case of compressed air respirators that no special logistics and additional apparatus components are necessary, unlike in the case of recycling respirators with $CO_2$ absorbers, which are correspondingly also more expensive. It would be advantageous especially in rescue and escape apparatuses if either the operating time with a given compressed air cylinder were prolonged, i.e., if it were possible to improve the utilization of a given compressed air reserve, or if it were possible to reduce the weight of the apparatus and to make it more easily portable at a given duration of use by reducing the size of the cylinder.

Rescue and escape apparatuses are carried directly on the body and shall therefore be, in general, relatively light-weight and easily portable, so that they are therefore especially well suited for the indicated purpose.

A compressed air respirator, which is also said to be used as a rescue apparatus, is known from GB 2 274 249 A. The compressed air flows here from a compressed air cylinder via an outlet at a constant gas volume flow into a breathing gas reservoir, from which the user of the apparatus breathes in via a mouthpiece and into which he also breathes out. Breathing gas enriched with $CO_2$ is released into the environment via an expiration valve, which opens when a preset pressure is reached in the breathing gas reservoir, while compressed air flows in continuously and at a constant rate from the compressed air cylinder.

The drawback of this prior-art device is that too much fresh breathing gas is made available to the user of the apparatus when he is under low to moderate physical strain due to the compressed air flowing in at a constant rate, at any rate more than is physiologically consumed, whereas a possibly substantially larger expiration volume will enter the breathing gas reservoir with increased $CO_2$ concentration under a higher physical strain, so that the mean $CO_2$ concentration of the gas being breathed in may increase to an undesirably high value. However, a higher setting of the constant gas volume flow into the breathing gas reservoir shortens the desired longer use time of the respirator. Efficient enrichment with $CO_2$ of the expired air released into the environment from the deep regions of the lung is not achieved with the prior-art respirator.

SUMMARY OF THE INVENTION

Thus, the object of the present invention is to provide a compressed air respirator with improved utilization of the compressed air reserve in case of compressed air consumption from the compressed air reserve that is proportional to the physical strain.

The object is accomplished with the features of claim 1.

An essential advantage of the compressed air respirator according to claim 1 is that by means of setting the volume of the reversible breathing gas reservoir, it is possible to optimize the rebreathed breathing gas with a possibly adapted mean $CO_2$ concentration as a function of the individual physical conditions of the user of the apparatus.

The subclaims show advantageous embodiments and variants of the compressed air respirator according to claim 1.

Exemplary embodiments of the present invention will be explained below on the basis of the schematic figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
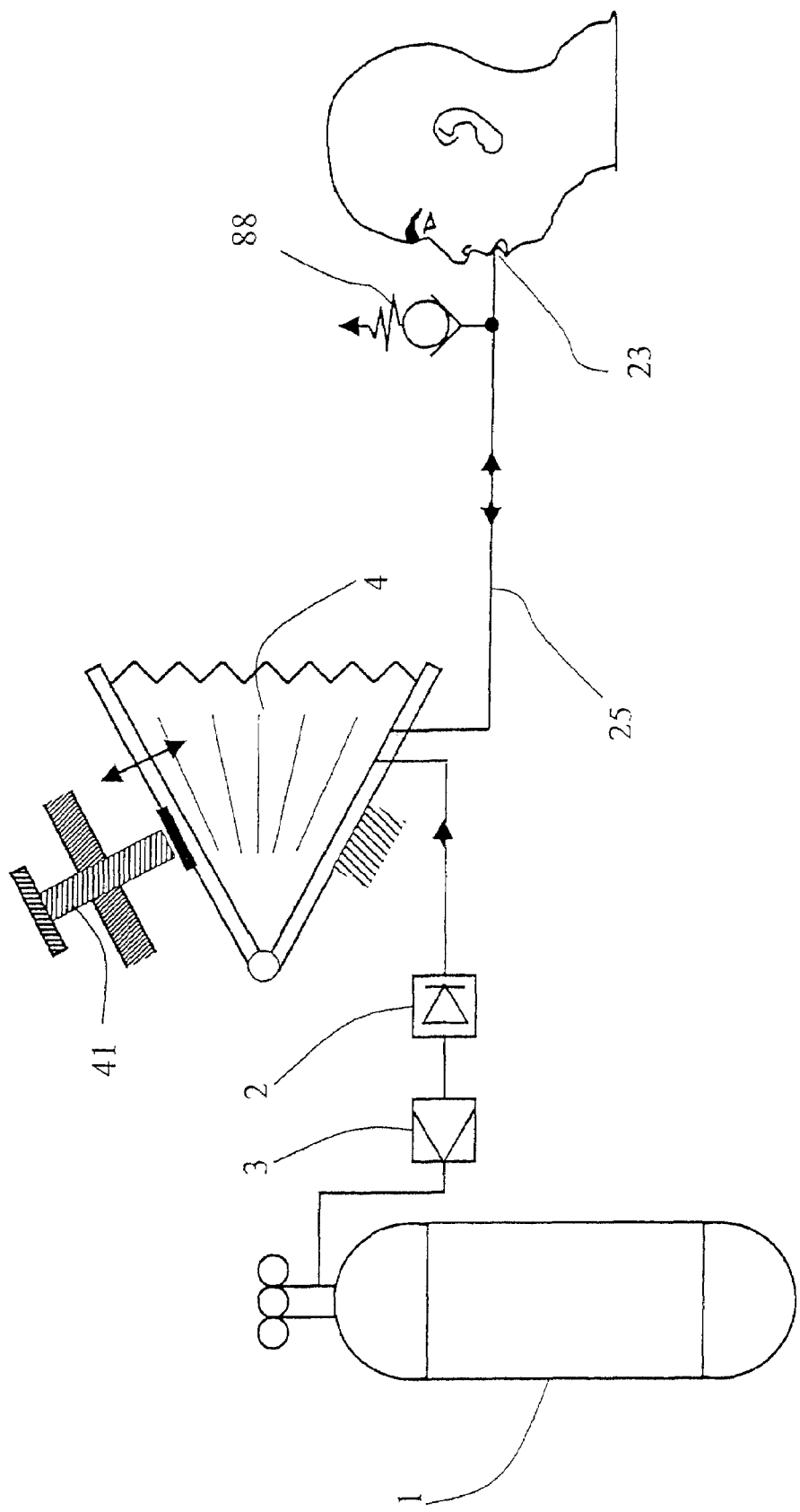
FIG. 1 shows a first simple embodiment of a compressed air respirator.

Referring to the drawings in particular, The device according to FIG. 1 with the user of the apparatus shown on the right has a compressed air reserve 1 with a demand air supply valve 2 and with a pressure reducer 3 arranged in between, wherein the demand air supply valve 2 is connected with a reversible breathing gas reservoir 4. The reversible breathing gas reservoir 4 is designed, for example, in the form of a breathing bellows, a cylinder, a bag or even a flexible tube.

The stop 41 is used to manually set the volume of the breathing gas reservoir 4 corresponding to the individual physical situation of the user of the device as will be explained below: The rebreathing line 25 for the user of the apparatus is operated, for example, by means of a mouthpiece 23 or alternatively via a mask, not shown, and is likewise connected with the breathing gas reservoir 4. The expiration valve 88 is preferably in the vicinity of the mouthpiece 23 or the mask in the rebreathing line 25 and opens to the environment when a preset pressure is exceeded in the rebreathing line 25.

The breathing by the user of the apparatus takes place via the compressed air respirator such that the demand air supply valve 2 opens during breathing in only when the breathing gas reservoir 4 is completely emptied. The user of the apparatus now breathes in from the demand air supply valve 2. During breathing out, the user of the apparatus pushes back the dead space and the connected, relatively low-$CO_2$ bronchial volume into the rebreathing line 25 until the breathing gas reservoir 4 strikes the adjustable stop 41 and opens the expiration valve 88 because of the overpressure building up. Air from the deep region of the lung with high $CO_2$ concentration is subsequently breathed out into the environment. During the subsequent breathing in following this, air with a relatively low $CO_2$ concentration from the connected bronchial volume and the dead space of the preceding breath is first breathed in from the rebreathing line 25 and the connected breathing gas reservoir 4 until the breathing gas reservoir 4 is again emptied, after which fresh air is breathed in via the demand air supply valve 2 and so on. The volume of the breathing gas reservoir 4 is thus set individually mechanically for the user of the apparatus, so that a high $CO_2$ ventilation is obtained at the same time with a mean $CO_2$ concentration in the inspiration air, equaling, for example, 1.5 vol. %, which is permissible for rescue purposes.

As an alternative, it is possible to set the volume for compressed air respirators that can be used during work, so that only so large a volume is rebreathed that a value specified for the maximum allowable workplace concentration of, for example, 0.5 vol. % for $CO_2$, is not exceeded.

Figure 2:
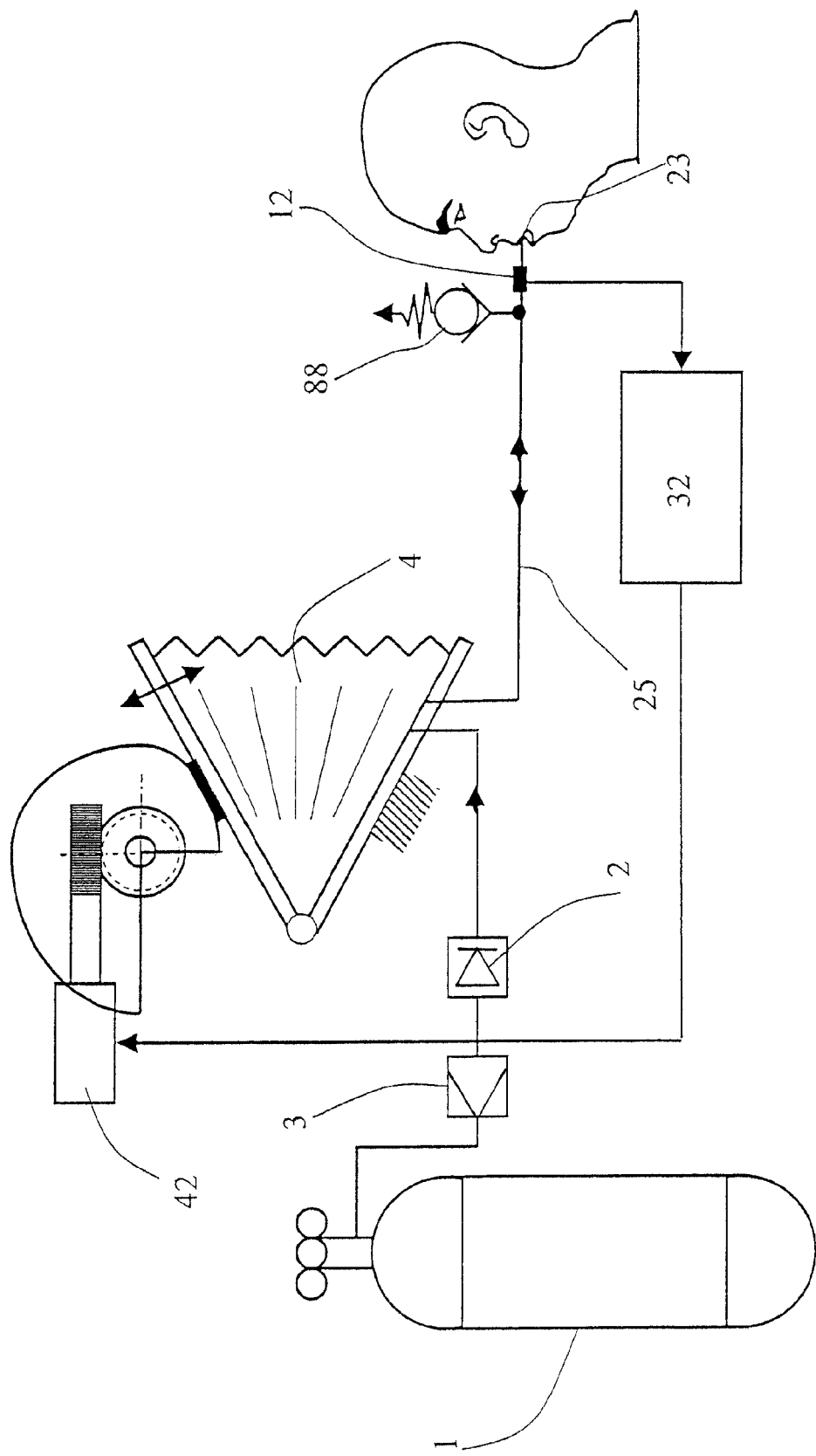
FIG. 2 shows a second embodiment of a compressed air respirator with electric setting of the breathing gas reservoir.
Figure 3:
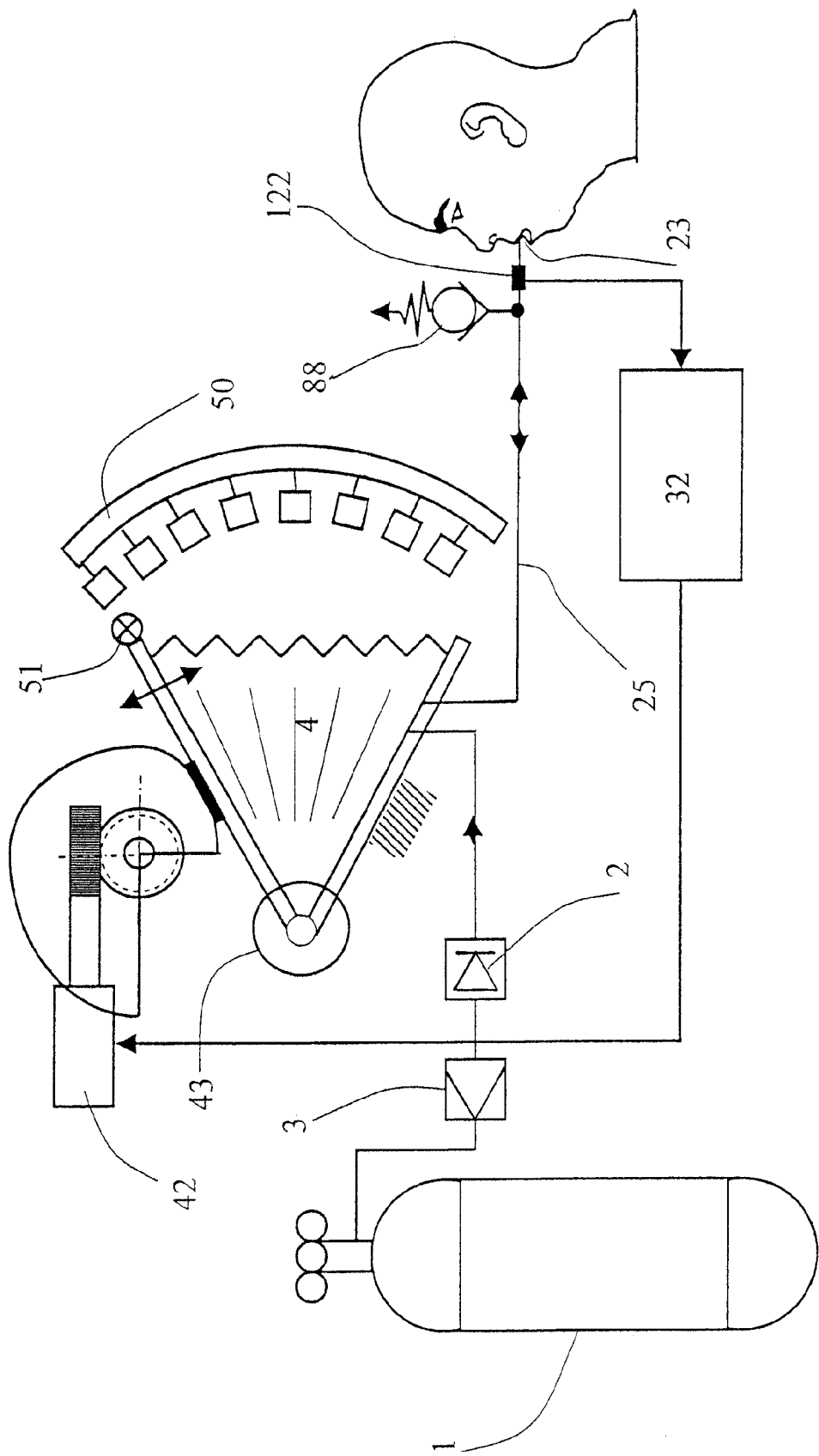
FIG. 3 shows a third embodiment of a compressed air respirator.

Since an exact manual setting of the most suitable volume of the breathing gas reservoir 4 is not possible for a reasonable rebreathing by the user of the apparatus, it is advantageous to provide a sensor-controlled regulation of the expansion volume of the breathing gas reservoir 4, as is shown in FIGS. 2 and 3.

FIG. 2 shows a combined sensor 12 for the $CO_2$ concentration and the breathing gas volume flow in the rebreathing line 25 on or next to the mouthpiece 23 of the user of the apparatus. The $CO_2$ volume flow, resolved for individual breaths, is detected and the volume of the breathing gas reservoir 4 is automatically adjusted for the rebreathing by means of a control unit 32 and an associated motor control 42 for the stop at the breathing gas reservoir 4 such that an average $CO_2$ concentration of a predetermined value of, e.g., 1.5 vol. % or 0.5 vol. % is obtained in the inspiration air. The motor control 42 acts on a worm drive for setting the distance.

FIG. 3 shows a device without the combined sensor 12 in FIG. 2, when this [sensor] would hinder the breathing function and if it is to be done away with because of the necessary power demand and the weight. The motion of the breathing gas reservoir 4 is scanned opto-electronically in the device according to FIG. 3 to determine the breathing gas volume flow at the beginning of inspiration and at the beginning of expiration.

An LED 51 is followed in FIG. 3 by means of a photodiode array 50 corresponding to the motion of the breathing gas reservoir 4. As an alternative, a path transducer or a shaft encoder 43, which has an optical or potentiometric design, may be used at the axis of the breathing gas reservoir 4.

The $CO_2$ sensor 122 used for the modulation of the $CO_2$ concentration taking place due to the inspiration and expiration is a simple, preferably infrared optical sensor without zero reference signal.

On the whole, automatic regulation of rebreathing with respect to physiologically optimal conditions becomes possible with a relatively simple device with a simple infrared sensor together with a means for scanning the motions of the breathing gas reservoir 4, an electronic control unit 32 and a motor control 42.

While specific embodiments of the invention have been shown and described in detail to illustrate the application of the principles of the invention, it will be understood that the invention may be embodied otherwise without departing from such principles.

What is claimed is:

1. A compressed air respirator apparatus, comprising:
a compressed air reserve with a connected demand air supply valve;
a reversible breathing gas reservoir with an adjustable volume, said demand air supply valve being connected with said reversible breathing gas reservoir to supply said reversible breathing gas reservoir with air;
a rebreathing line with a user connection for the user of the apparatus, said rebreathing line having an expiration valve for expiring exhaled breathing air from said rebreathing line to the respirator environment when gas pressure in said breathing line is above a preset pressure, said rebreathing line being in bi-directional flow connection with gas in said breathing gas reservoir such that gas pressure in said reversible breathing gas reservoir is the same as said gas pressure in said breathing line;
a motor operatively connected to said reversible breathing gas reservoir to change the volume thereof;
a motor control wherein the volume of said breathing gas reservoir is set by means of said motor controlled by said motor control;
a control unit; and
a combined sensor for $CO_2$ concentration and breathing gas volume flow, said combined sensor being arranged in said rebreathing line, said combined sensor being connected with said control unit and said motor control such that depending on a breath-resolved $O_2$ volume flow determined by means of said combined sensor, the volume for rebreathing from said breathing gas reservoir is regulated by means of said motor control such that a $CO_2$ concentration level stored in said control unit is obtained, on average, for rebreathing.

2. A compressed air respirator apparatus comprising:
a compressed air reserve with a connected demand air supply valve;
a reversible breathing gas reservoir with an adjustable volume, said demand air supply valve being connected with said reversible breathing gas reservoir to supply said reversible breathing gas reservoir with air;
a rebreathing line with a user connection for the user of the apparatus, said rebreathing line having an expiration valve for expiring exhaled breathing air from said rebreathing line to the respirator environment when gas pressure in said breathing line is above a preset pressure, said rebreathing line being in two way flow connection with gas in said breathing gas reservoir such that gas pressure in said reversible breathing gas reservoir is the same as said gas pressure in said breathing line;
a motor operatively connected to said reversible breathing gas reservoir to change the volume thereof;
a motor control wherein said breathing gas reservoir has a volume set by means of said motor controlled by said motor control;
an opto-electronic registering means for detecting the motion of said reversible breathing gas reservoir;
a control unit; and
a $CO_2$ sensor connected with said motor control, said $CO_2$ sensor being arranged in said rebreathing line, said control unit being connected with said opto-electronic registering means for detecting the motion of said reversible breathing gas reservoir, said motor control being actuated for setting rebreathing by varying the volume of said breathing gas reservoir as a function of measured $CO_2$ concentration and the motion of said breathing gas reservoir.

3. A compressed air respirator apparatus comprising:

a compressed air reserve with a connected demand air supply valve;

a reversible breathing gas reservoir with an adjustable volume, said demand air supply valve being connected with said reversible breathing gas reservoir to supply said reversible breathing gas reservoir with air;

a rebreathing line with a user connection for the user of the apparatus, said rebreathing line having an expiration valve for expiring exhaled breathing air from said rebreathing line to the respirator environment when gas pressure in said breathing line is above a preset pressure, said rebreathing line being in direct two way flow connection with gas in said breathing gas reservoir such that gas pressure in said reversible breathing gas reservoir is the same as the gas pressure in said breathing line;

a motor operatively connected to said reversible breathing gas reservoir to change the volume thereof;

a motor control wherein said breathing gas reservoir has a volume set by means of said motor controlled by said motor control;

a control unit operatively connected to said motor control;

a path transducer or shaft encoder for detecting the motion of said reversible breathing gas reservoir; and a $CO_2$ sensor connected with said motor control via said control unit, said $CO_2$ sensor being arranged in said rebreathing line, said control unit being connected with said path transducer or shaft encoder for detecting the motion of said reversible breathing gas reservoir, so that said motor control is actuated for setting the rebreathing by varying the volume of said breathing gas reservoir as a function of a measured $CO_2$ concentration and the motion of said breathing gas reservoir.

* * * * *